United States Patent
Kuwabara

(10) Patent No.: US 12,023,307 B2
(45) Date of Patent: Jul. 2, 2024

(54) COMMON COLD SYMPTOM RELIEVING AGENT

(71) Applicant: THERAVALUES CORPORATION, Tokyo (JP)

(72) Inventor: Yoshitaka Kuwabara, Chiyoda-ku (JP)

(73) Assignee: THERAVALUES CORPORATION, Tokyo (JP)

( * ) Notice: Subject to any disclaimer, the term of this patent is extended or adjusted under 35 U.S.C. 154(b) by 0 days.

(21) Appl. No.: 18/062,107

(22) Filed: Dec. 6, 2022

(65) Prior Publication Data

US 2024/0091173 A1    Mar. 21, 2024

(30) Foreign Application Priority Data

Sep. 15, 2022 (JP) ................ 2022-147139

(51) Int. Cl.
*A61K 31/12* (2006.01)
*A61K 9/00* (2006.01)
*A61P 31/16* (2006.01)

(52) U.S. Cl.
CPC ............ *A61K 31/12* (2013.01); *A61K 9/0053* (2013.01); *A61P 31/16* (2018.01)

(58) Field of Classification Search
CPC ..................................................... A61K 31/12
See application file for complete search history.

(56) References Cited

U.S. PATENT DOCUMENTS

| 8,545,903 B2 * | 10/2013 | Lee ............ A23L 27/14 424/725 |
| 10,987,329 B1 * | 4/2021 | Raju ............ A61K 36/9066 |
| 2020/0360300 A1 * | 11/2020 | Sordillo .......... A61K 31/20 |

FOREIGN PATENT DOCUMENTS

| JP | 2008-280333 A | 11/2008 |
| JP | 2009-263638 A | 11/2009 |
| JP | 2016-535028 A | 11/2016 |
| WO | WO 2015/174475 A1 | 11/2015 |
| WO | WO 2019/160146 A1 | 8/2019 |

OTHER PUBLICATIONS

Dynamic turmeric by Stonehenge Health.*
Saber-Moghaddam, N. et al., "Oral Nano-Curcumin Formulation Efficacy in Management of Mild to Moderate Hospitalized Coronavirus Disease-19 Patients: An Open Label Nonrandomized Clinical Trial", Phytotherapy Research, John Wiley & Sons, Ltd. 2021, 8 pages.
Wu, S. et al., "Effect of Curcumin on Nasal Symptoms and Airflow in Patients with Perennial Allergic Rhinitis", American College of Allergy, Asthma & Immunology, Ann Allergy Asthma Immunol, vol. 117, 2016, 7 pages.
International Search Report and Written Opinion dated Dec. 5, 2023, for International Application No. PCT/JP2023/033485 (with a machine translation of the Written Opinion).
Dony Mathew, et al., "Antiviral potential of curcumin", Journal of Functional Foods, vol. 40, Jan. 2018, pp. 692-699.
Abdollah Ardebili, et al., "Antiviral Therapeutic Potential of Curcumin: An Update", Molecules, 2021, 26(22), 6994, pp. 1-23.
G.K. Jayaprakasha, et al., "Chemistry and biological activities of C. longa", Trends in Food Science & Technology, 2005, 16(12), pp. 533-548.

* cited by examiner

*Primary Examiner* — Rei Tsang Shiao
(74) *Attorney, Agent, or Firm* — Oblon, McClelland, Maier & Neustadt, L.L.P.

(57) ABSTRACT

To reveal which curcumin preparation, among various existing curcumin preparations, is effective for various symptoms of a common cold.

Provided is an agent for relieving common cold symptom which contains, as an active ingredient, a curcumin-containing composition that contains fine particles of curcumin or turmeric pigment, or a mixture containing curcumin or turmeric pigment containing an amorphous thereof and a cellulose derivative.

14 Claims, No Drawings

COMMON COLD SYMPTOM RELIEVING AGENT

TECHNICAL FIELD

The present invention relates to a common cold symptom relieving agent.

BACKGROUND ART

A cold (common cold) is a viral upper respiratory infection caused by a variety of viruses, such as rhinoviruses, adenoviruses, coronaviruses, enteroviruses, influenza viruses, parainfluenza viruses, and respiratory syncytial viruses. In a mild cold, local symptoms of the nose and throat are presented, and in a severe cold, systemic symptoms accompanied by fever and muscle pain are presented. The cold syndrome is difficult to determine both subjectively and objectively, and many of the cold syndromes are expressed in different terms such as sinusitis, otitis media, laryngitis, tonsillitis, and pharyngitis, which are complications of the cold syndrome.

Therefore, as a therapeutic agent for a cold (common cold), a cold remedy containing a non-steroidal anti-inflammatory agent, an antihistamine, an anticholinergic agent, a sympathetic nerve stimulator, an antitussive agent, a bronchodilator, an expectorant, and the like is used. Since these cold remedies contain many components, there are concerns about various side effects.

Meanwhile, it is known that curcumin has an anti-inflammatory activity and an inhibitory activity on the release of various inflammatory cytokines, and thus it is suggested that curcumin may be effective for ameliorating rhinitis symptoms and treating allergic rhinitis (NPLs 1 and 2).

CITATION LIST

Non Patent Literature

[NPL 1] Phytotherapy Research, 2021: 1-8
[NPL 2] Ann Allergy Asthma Immunol 117(2016) 697-702

SUMMARY OF INVENTION

Technical Problem

However, it is still unclear how effective curcumin is for the above-mentioned various symptoms of a common cold.

An object of the present invention is to reveal which curcumin preparation, among various existing curcumin preparations, is effective for various symptoms of a common cold.

Solution to Problem

Therefore, the present inventor conducted a randomized, placebo-controlled, double-blind, parallel group comparative test using two types of curcumin preparations, and found that the two types of curcumin preparations reduce the incidence of various symptoms of a common cold and are useful as common cold symptom relieving agents, thereby completing the present invention.

That is, the present invention provides the following inventions [1] to [8].

[1] An agent for relieving a symptom from a common cold, the agent containing, as an active ingredient, a curcumin-containing composition that contains fine particles of curcumin or turmeric pigment, or a mixture containing curcumin or turmeric pigment containing an amorphous thereof and a cellulose derivative.

[2] The agent according to [1], wherein the symptom from a cold is selected from the group consisting of whole body malaise, chilliness, feverishness, fatigue, sneezing, nasal discharge, blocked nose, throat pain, cough, joint pain, and muscle pain.

[3] The agent according to [1], which contains from 90 mg to 300 mg of curcumin in an oral dose per day for an adult.

[4] The agent according to [2], which contains from 90 mg to 300 mg of curcumin in an oral dose per day for an adult.

[5] A method for relieving a symptom from a common cold, the method including administering a composition containing (a) fine particles of curcumin or turmeric pigment, or (b) curcumin or turmeric pigment containing an amorphous thereof and a cellulose derivative.

[6] The method according to [5], wherein the symptom from a common cold is selected from the group consisting of whole body malaise, chilliness, feverishness, fatigue, sneezing, nasal discharge, blocked nose, throat pain, cough, joint pain, and muscle pain.

[7] The method according to [5], wherein the composition contains from 90 mg to 300 mf of curcumin in an oral dose per day for an adult.

[8] The method according to [6], wherein the composition contains from 90 mg to 300 mf of curcumin in an oral dose per day for an adult.

Advantageous Effects of Invention

Oral administration of the curcumin-containing composition of the present invention reliably reduces the onset of multiple symptoms from a cold, and accelerates recovery from the cold since there are almost no side effects.

DESCRIPTION OF EMBODIMENTS

The agent for relieving common cold symptom of the present invention is a common cold symptom relieving agent containing, as active ingredient, a curcumin-containing composition that contains curcumin or turmeric pigment, and one aspect of the present invention is a common cold symptom relieving agent containing, as an active ingredient, a curcumin-containing composition that contains (a) fine particles of curcumin or turmeric pigment, or (b) a mixture of curcumin or turmeric pigment containing an amorphous thereof, and a cellulose derivative.

A preferred curcumin-containing composition is the component (a) fine particles of curcumin or turmeric pigment, or the component (b) a mixture of curcumin or turmeric pigment containing an amorphous thereof, and a cellulose derivative.

The component (a) fine particles of curcumin or turmeric pigment is preferably curcumin or turmeric pigment having an average particle diameter (median diameter: d50) of 1 μm or less, and is more preferably a composition described in JP-B-5448511, which contains gum ghatti and curcumin or turmeric pigment having an average particle diameter of 1 m or less. Here, the average particle diameter of curcumin or turmeric pigment is more preferably 0.9 μm or less, still more preferably 0.5 μm or less, and even more preferably 0.1 to 0.5 μm.

In the composition containing gum ghatti and curcumin or turmeric pigment having an average particle diameter of 1 μm or less, it is preferable that gum ghatti is contained in an amount of 10 to 100 parts by mass with respect to 100 parts by mass of curcumin or turmeric pigment.

Examples of the component (b) a mixture of curcumin or turmeric pigment containing an amorphous thereof, and a cellulose derivative include (b-1) a composition of a solid curcumin or a turmeric pigment containing an amorphous thereof and a water-soluble cellulose derivative in a simply uniformly mixed state, and (b-2) a composition of a solid curcumin or a turmeric pigment containing an amorphous thereof, hydroxypropyl methyl cellulose, and a non-gel-forming pharmaceutical additive in a simply uniformly mixed state.

As the component (b-1) a composition of a solid curcumin or a turmeric pigment containing an amorphous thereof and a water-soluble cellulose derivative in a simply uniformly mixed state, for example, the following composition described in JP-B-7072905 is preferable: a composition that contains, in a simply uniformly mixed state, (A) a solid curcumin or a turmeric pigment containing an amorphous thereof, and (B) one or more solid water-soluble polymers that are viscous in an aqueous medium having a pH of 5 or more, and are selected from the group consisting of hydroxypropyl cellulose, hydroxypropyl methyl cellulose, carboxymethyl cellulose, sodium carboxymethyl cellulose, methyl cellulose, hydroxypropyl methyl cellulose acetate succinate, carboxymethyl ethyl cellulose, and hydroxypropyl methyl cellulose phthalate, and in which the ratio of (A-1) a crystalline of the component (A) curcumin or turmeric pigment to (A-2) an amorphous of the component (A) curcumin or turmeric pigment, that is, (A-1)/(A-2) is 0.67 or less.

Here, the content mass ratio of the component (A) curcumin or turmeric pigment to the component (B) a water-soluble cellulose derivative, that is, (A)/(B) is preferably 0.1 to 570, and more preferably 0.5 to 50. In addition, the average particle diameters (d50) of the curcumin or turmeric pigment and the water-soluble cellulose derivative are preferably each 300 m or less.

As the component (b-2) a composition containing a solid curcumin or a turmeric pigment containing an amorphous thereof, hydroxypropyl methyl cellulose, and a non-gel-forming pharmaceutical additive in a simply uniformly mixed state, for example, the following composition described in JP-B-7080504 is preferable: a composition that contains, in a simply uniformly mixed state, (A) one or more selected from the group consisting of a solid curcumin and a turmeric pigment containing an amorphous thereof, (B) hydroxypropyl methyl cellulose having, as a 2% by mass aqueous solution, a viscosity at 20° C. of 1 mm$^2$/s or more and 10 mm$^2$/s or less, and (C) a non-gel-forming pharmaceutical additive, and in which the content mass ratio of the component (C) to a sum of the component (A) and the component (B), that is, ((C)/[(A)+(B)]) is 0.4 to 7.

Here, the content mass ratio of the component (A) curcumin or turmeric pigment to the component (B) hydroxypropyl methyl cellulose, that is, (A)/(B) is preferably 0.1 to 2. Examples of the non-gel-forming pharmaceutical additive include one or more selected from the group consisting of non-gel-forming excipients, non-gel-forming disintegrants, non-gel-forming dispersants, non-gel-forming lubricants, non-gel-forming colorants, non-gel-forming perfumes, and non-gel-forming flavoring agents.

Examples of the non-gel-forming excipient include one or more selected from the group consisting of lactose, fructose, crystalline cellulose, corn starch, dextrin, maltodextrin, isomalt, inositol, casein, fructose, xylitol, calcium citrate, citric acid hydrate, sodium citrate, purified sucrose, sorbitol, calcium carbonate, trehalose, potato starch, hydroxypropyl starch, glucose, partially pregelatinized starch, pullulan, pectin, povidone, maltose hydrate, mannitol, anhydrous citric acid, anhydrous sodium citrate, and anhydrous lactose.

Examples of the non-gel-forming disintegrant include one or more selected from the group consisting of dextrin, crospovidone, croscarmellose, croscarmellose sodium, crystalline cellulose, partially pregelatinized starch, and povidone.

Examples of the non-gel-forming dispersant include one or more selected from the group consisting of gum arabic, carrageenan, refined soybean lecithin, tragacanth powder, and gum ghatti.

Examples of the non-gel-forming lubricant include one or more selected from the group consisting of magnesium stearate, calcium stearate, light anhydrous silicic acid, silicon dioxide, and talc.

The non-gel-forming colorant is a commonly used colorant, and examples thereof include food dyes, caramel, and iron oxides.

The non-gel-forming perfume is a commonly used perfume, and examples thereof include various flavors and various extracts.

The non-gel-forming flavoring agent is a commonly used flavoring agent, and examples thereof include ascorbic acids, citric acids, and various sweeteners.

The form of the curcumin-containing composition is preferably a form of a common composition for oral administration, and specific examples thereof include powders, powdered materials, granules, pills, capsules, tablets (including uncoated tablets, sugar-coated tablets, orally rapidly disintegrating tablets, chewable tablets, effervescent tablets, troches, film-coated tablets, and the like), dry syrups, films, and jellies.

These forms can be prepared by appropriately blending, in addition to the curcumin-containing composition, a carrier, a base, and/or an additive commonly used in the field of pharmaceutical preparations within a range in which the object of the present invention is achieved.

For example, magnesium stearate, calcium stearate, or the like may be blended as a lubricant, and corn starch or the like may be blended as a space filler. In addition, it is preferable to use dextrin, crospovidone, carmellose, carmellose calcium, croscarmellose sodium, low-substituted hydroxypropyl cellulose, crystalline cellulose, or the like that act as a disintegrant. Among these additives, disintegrants are preferably added, and dextrin, crospovidone, carmellose, carmellose calcium, croscarmellose sodium, low-substituted hydroxypropyl cellulose, or crystalline cellulose is preferably used.

As described in Examples below, the curcumin-containing composition has an action of relieving various common cold symptoms, and is useful as a common cold symptom relieving agent.

The wording "relieving common cold symptoms" may encompass both reducing the onset of common cold symptoms and relieving the existing common cold symptoms.

Examples of the common cold symptoms may include one or more symptoms selected from the group consisting of whole body malaise, chilliness, feverishness, fatigue, sneezing, nasal discharge, blocked nose, throat pain, cough, joint pain, and muscle pain.

Since curcumin or turmeric pigment has high safety, the agent for relieving common cold symptom of the present invention may not cause side effects, unlike a conventional combination cold remedy, is safe, and can be continually orally taken.

The agent for relieving common cold symptom of the present invention is preferably orally administered, and the dose thereof can be appropriately changed depending on body weight, age, and the like, but it is usually preferable that 90 mg to 300 mg of the agent in terms of the amount of curcumin is administered to an adult in 1 to 3 divided doses per day.

EXAMPLES

In the following, the present invention is described in more detail with reference to examples, but the present invention is not limited to these examples at all.

Example 1

(1) Test Design

Healthy Japanese adult men and women were subjected to a randomized, placebo-controlled, double-blind, parallel group comparative test.

As the preparation for administration, 150 mg (as curcumin contents)/day of Theracurmin® Super (TS-P1) or 150 mg (as curcumin contents)/day of Theracurmin® (CR-033P) was continually taken for 12 weeks.

Here, Theracurmin® Super contains, in a 37.5 mg capsule, 125 mg of TS-P1 powder, maltodextrin, and calcium stearate, and 4 capsules were taken in 2 divided doses per day in the morning and evening.

The TS-P1 powder is formed of a mixture of amorphous curcumin, HPMC, and maltodextrin.

Theracurmin® contains, in a 37.5 mg capsule, 125 mg of CR-033P powder, corn starch, calcium stearate, and fine silicon dioxide, and 4 capsules were taken in 2 divided doses per day in the morning and evening.

The CR-033P powder is formed of curcumin, gum ghatti, citric acid, maltodextrin, and maltose (average particle diameter: 0.19 μm).

(2) Evaluation Item

A common cold symptom investigation was performed.

(3) Results

The cumulative number of days with the common cold symptoms (the total of number of days of symptoms including "whole body malaise", "chilliness", "feverishness", "fatigue", "sneezing", "nasal discharge", "blocked nose", "throat pain", "cough", "joint pain", and "muscle pain") per test participant during the test period, which is the main outcome of the test, and the maximum duration of the day with each common cold symptoms (the total of number of days of the maximum duration of symptoms including "whole body malaise", "chilliness", "feverishness", "fatigue", "sneezing", "nasal discharge", "blocked nose", "throat pain", "cough", "joint pain", and "muscle pain") per test participant during the test period are shown in Tables 1 to 3.

TABLE 1

The cumulative number and maximum duration of expression days with the common cold symptoms during the intervention period per subject in PPS analysis

| | TS-P1 group | | CR-033P group | | Placebo group | | Group comparison (TS-P1 group − Placebo group) | | | | | Group comparison (CR-033P group − Placebo group) | | | | |
|---|---|---|---|---|---|---|---|---|---|---|---|---|---|---|---|---|
| | Mean | SD | Mean | SD | Mean | SD | Group difference | SE | 95% CI− | 95% CI+ | p value | Group difference | SE | 95% CI− | 95% CI+ | p value |
| The cumulative number of expression | 38.6 ± | 33.8 | 39.4 ± | 34.7 | 56.8 ± | 32.0 | −18.2 | 8.5 | −35.1 | −1.2 | 0.036* | −17.4 | 8.5 | −34.3 | −0.6 | 0.042* |
| The maximum duration of expression | 22.3 ± | 30.2 | 27.8 ± | 33.1 | 45.2 ± | 34.7 | −22.9 | 8.3 | −39.4 | −6.4 | 0.007** | −17.4 | 8.2 | −33.8 | −1.0 | 0.037* |

Note:
Values are shown as mean ± standard deviation (SD), group differences, and standard error (SE) and 95% confidence interval (95% CI) for group differences. The cumulative number of days with the common cold symptoms which was defined as the onset of more than one of the each symptoms ("whole body malaise", "feverishness", "fatigue", "sneezing", "nasal discharge", "blocked nose", "throat pain", "cough", "joint pain", "muscle pain"), while the maximum duration of expression days with the common cold symptoms (defined as the total of the maximum duration of the days with each symptom).
†, Primary outcome,
*p < 0.05,
**p < 0.01

TABLE 2

The cumulative number and maximum duration of expression days with each symptom during the intervention period per subject in PPS analysis

| Symptoms | | TS-P1 group (n = 32) | | CR-033P group (n = 33) | | Placebo group (n = 30) | |
|---|---|---|---|---|---|---|---|
| | | Mean | SD | Mean | SD | Mean | SD |
| Whole body malaise | The cumulative number of expression days | 14.1 ± | 23.8 | 17.1 ± | 30.5 | 21.9 ± | 33.1 |
| | The maximum duration of expression days | 7.9 ± | 20.5 | 10.0 ± | 21.8 | 15.6 ± | 27.2 |
| Chilliness | The cumulative number of expression days | 2.7 ± | 8.6 | 7.0 ± | 15.0 | 4.8 ± | 10.8 |
| | The maximum duration of expression days | 0.9 ± | 1.8 | 3.0 ± | 7.3 | 2.6 ± | 6.8 |

TABLE 2-continued

The cumulative number and maximum duration of expression days with each symptom during the intervention period per subject in PPS analysis

| Symptoms | | TS-P1 group (n = 32) Mean ± SD | | CR-033P group (n = 33) Mean ± SD | | Placebo group (n = 30) Mean ± SD | |
|---|---|---|---|---|---|---|---|
| Feverishness | The cumulative number of expression days | 1.8 ± | 3.9 | 2.8 ± | 6.8 | 5.1 ± | 11.4 |
|  | The maximum duration of expression days | 0.9 ± | 1.4 | 1.1 ± | 2.0 | 2.6 ± | 7.5 |
| Fatigue | The cumulative number of expression days | 25.8 ± | 30.2 | 27.8 ± | 33.2 | 31.3 ± | 33.2 |
|  | The maximum duration of expression days | 10.1 ± | 17.5 | 14.7 ± | 25.2 | 16.2 ± | 22.0 |
| Sneezing | The cumulative number of expression days | 7.9 ± | 14.9 | 13.2 ± | 20.4 | 18.4 ± | 18.6 |
|  | The maximum duration of expression days | 3.6 ± | 8.3 | 7.2 ± | 15.4 | 8.9 ± | 12.9 |
| Nasal discharge | The cumulative number of expression days | 9.8 ± | 14.8 | 19.8 ± | 29.2 | 24.4 ± | 30.4 |
|  | The maximum duration of expression days | 4.2 ± | 8.3 | 12.4 ± | 19.8 | 15.6 ± | 22.3 |
| Blocked nose | The cumulative number of expression days | 3.0 ± | 5.1 | 10.5 ± | 21.6 | 14.2 ± | 25.6 |
|  | The maximum duration of expression days | 1.8 ± | 3.9 | 7.8 ± | 17.6 | 10.1 ± | 19.9 |
| Throat pain | The cumulative number of expression days | 5.0 ± | 8.1 | 3.4 ± | 7.0 | 6.0 ± | 14.7 |
|  | The maximum duration of expression days | 1.9 ± | 2.8 | 1.7 ± | 3.3 | 3.4 ± | 8.9 |
| Cough | The cumulative number of expression days | 2.6 ± | 8.6 | 3.6 ± | 10.7 | 9.0 ± | 17.1 |
|  | The maximum duration of expression days | 1.0 ± | 2.6 | 2.6 ± | 9.0 | 4.1 ± | 8.6 |
| Joint pain | The cumulative number of expression days | 6.9 ± | 20.8 | 6.9 ± | 20.3 | 7.9 ± | 21.5 |
|  | The maximum duration of expression days | 5.0 ± | 16.9 | 5.9 ± | 20.2 | 6.7 ± | 19.1 |
| Muscle pain | The cumulative number of expression days | 8.3 ± | 20.2 | 9.2 ± | 20.1 | 11.4 ± | 24.1 |
|  | The maximum duration of expression days | 4.8 ± | 15.6 | 5.8 ± | 16.5 | 8.1 ± | 20.0 |

TABLE 3

The cumulative number and maximum duration of expression days with each symptom during the intervention period per subject in PPS analysis

| Symptom | | Group comparison (TS-P1 group − Placebo group) | | | | | Group comparison (CR-033P group − Placebo group) | | | | |
|---|---|---|---|---|---|---|---|---|---|---|---|
| | | Group difference | SE | 95% CI− | 95% CI+ | p value | Group difference | SE | 95% CI− | 95% CI+ | p value |
| Whole body malaise | The cumulative number of expression days | −7.8 | 7.5 | −22.6 | 7.0 | 0.296 | −4.8 | 7.4 | −19.5 | 9.8 | 0.514 |
|  | The maximum duration of expression days | −7.7 | 5.9 | −19.5 | 4.0 | 0.194 | −5.6 | 5.9 | −17.3 | 6.0 | 0.342 |
| Chilliness | The cumulative number of expression days | −2.1 | 3.0 | −8.1 | 3.8 | 0.477 | 2.2 | 3.0 | −3.7 | 8.1 | 0.463 |
|  | The maximum duration of expression days | −1.7 | 1.5 | −4.7 | 1.3 | 0.259 | 0.4 | 1.5 | −2.5 | 3.4 | 0.770 |
| Feverishness | The cumulative number of expression days | −3.3 | 2.0 | −7.3 | 0.7 | 0.104 | −2.3 | 2.0 | −6.3 | 1.6 | 0.241 |
|  | The maximum duration of expression days | −1.7 | 1.1 | −3.9 | 0.6 | 0.146 | −1.5 | 1.1 | −3.8 | 0.7 | 0.175 |
| Fatigue | The cumulative number of expression days | −5.5 | 8.2 | −21.8 | 10.7 | 0.502 | −3.5 | 8.1 | −19.6 | 12.7 | 0.672 |
|  | The maximum duration of expression days | −6.1 | 5.5 | −17.1 | 4.9 | 0.273 | −1.6 | 5.5 | −12.5 | 9.4 | 0.777 |
| Sneezing | The cumulative number of expression days | −10.5 | 4.6 | −19.6 | −1.3 | 0.026* | −5.2 | 4.6 | −14.2 | 3.9 | 0.263 |
|  | The maximum duration of expression days | −5.3 | 3.2 | −11.7 | 1.0 | 0.099 | −1.8 | 3.2 | −8.1 | 4.6 | 0.583 |
| Nasal discharge | The cumulative number of expression days | −14.5 | 6.5 | −27.5 | −1.5 | 0.029* | −4.6 | 6.5 | −17.5 | 8.3 | 0.483 |
|  | The maximum duration of expression days | −11.4 | 4.5 | −20.4 | −2.5 | 0.013* | −3.2 | 4.5 | −12.1 | 5.7 | 0.480 |
| Blocked nose | The cumulative number of expression days | −11.2 | 4.9 | −21 | −1.4 | 0.026* | −3.6 | 4.9 | −13.4 | 6.1 | 0.462 |
|  | The maximum duration of expression days | −8.4 | 3.9 | −16.1 | −0.6 | 0.036* | −2.3 | 3.9 | −10 | 5.4 | 0.544 |
| Throat pain | The cumulative number of expression days | −1.1 | 2.6 | −6.3 | 4.2 | 0.687 | −2.6 | 2.6 | −7.8 | 2.6 | 0.315 |
|  | The maximum duration of expression days | −1.5 | 1.4 | −4.3 | 1.3 | 0.296 | −1.7 | 1.4 | −4.5 | 1.1 | 0.222 |
| Cough | The cumulative number of expression days | −6.4 | 3.2 | −12.7 | −0.1 | 0.047* | −5.5 | 3.2 | −11.7 | 0.8 | 0.088 |
|  | The maximum duration of expression days | −3.1 | 1.9 | −6.8 | 0.6 | 0.097 | −1.5 | 1.9 | −5.2 | 2.2 | 0.423 |
| Joint pain | The cumulative number of expression days | −1 | 5.3 | −11.5 | 9.6 | 0.856 | −1 | 5.3 | −11.5 | 9.4 | 0.847 |
|  | The maximum duration of expression days | −1.7 | 4.8 | −11.2 | 7.8 | 0.718 | −0.8 | 4.7 | −10.2 | 8.7 | 0.873 |
| Muscle pain | The cumulative number of expression days | −3.1 | 5.5 | −13.9 | 7.7 | 0.573 | −2.3 | 5.4 | −13 | 8.5 | 0.674 |
|  | The maximum duration of expression days | −3.3 | 4.4 | −12.1 | 5.5 | 0.460 | −2.3 | 4.4 | −11.1 | 6.4 | 0.595 |

Note:
Values are shown as mean ± standard deviation (SD), group differences, and standard error (SE) and 95% confidence interval (95% CI) for group differences.
*p < 0.05

The cumulative number of days for which common cold symptoms persisted during the intervention period for each subject was 56.8±32.0 days in the placebo group, 38.6±33.8 days in the TS-P1 group (group difference from the placebo group −18.2 days, 95% CI [−35.1, −1.2]), and 39.4±34.7 days in the CR-033P group (group difference from the placebo group −17.4 days, 95% CI [−34.3, −0.6]). The maximum number of days for which common cold symptoms persisted during the study period for each subject was 45.2±34.7 days in the placebo group, 22.3±30.2 days in the TS-P1 group (group difference from the placebo group −22.9 days, 95% CI [−39.4, −6.4]), and 27.8±33.1 days in the CR-033P group (group difference from the placebo group −17.4 days, 95% CI [−33.8, −1.0]). The cumulative and maximum number of days for which common cold symptoms persisted were significantly lower in the TS-P1 and CR-033P groups than those in the placebo group.

Furthermore, the cumulative number of days for which sneezing (group difference from the placebo group −10.5 days, 95% CI [−19.6, −1.3]), nasal discharge (group difference from the placebo group −14.5 days, 95% CI [−27.5, −1.5]), blocked nose (group difference from the placebo group −11.2 days, 95% CI [−21.0, −1.4]), and cough (group difference from the placebo group—, 95% CI [−12.7, −0.1]) persisted was significantly shorter in the TS-P1 group than that in the placebo group.

Collectively, the data above indicate that intake of TS-P1 and CR-033P (150 mg/day as curcumin contents, respectively) reduced common cold symptoms. In particular, TS-P1 ameliorated local symptoms, such as sneezing, nasal discharge, nasal obstruction, and cough.

The invention claimed is:

1. An agent for relieving a symptom from a common cold, the agent comprising, as an active ingredient, a curcumin-containing composition that contains fine particles of amorphous curcumin and a water-soluble cellulose derivative,
wherein the water-soluble cellulose derivative is selected from the group consisting of: hydroxypropyl cellulose, hydroxypropyl methyl cellulose, carboxymethyl cellulose, sodium carboxymethyl cellulose, methyl cellulose.

2. The agent according to claim 1, wherein the symptom from a cold is selected from the group consisting of whole body malaise, chilliness, feverishness, fatigue, sneezing, nasal discharge, blocked nose, throat pain, cough, joint pain, and muscle pain.

3. The agent according to claim 1, which comprises from 90 mg to 300 mg of curcumin in an oral dose per day for an adult.

4. The agent according to claim 2, which comprises from 90 mg to 300 mg of curcumin in an oral dose per day for an adult.

5. A method for relieving a symptom from a common cold, the method comprising administering a composition comprising fine particles of amorphous curcumin and a water-soluble cellulose derivative,
wherein the water-soluble cellulose derivative is selected from the group consisting of: hydroxypropyl cellulose, hydroxypropyl methyl cellulose, carboxymethyl cellulose, sodium carboxymethyl cellulose, methyl cellulose.

6. The method according to claim 5, wherein the symptom from a common cold is selected from the group consisting of whole body malaise, chilliness, feverishness, fatigue, sneezing, nasal discharge, blocked nose, throat pain, cough, joint pain, and muscle pain.

7. The method according to claim 5, wherein the composition comprises from 90 mg to 300 mg of curcumin in an oral dose per day for an adult.

8. The method according to claim 6, wherein the composition comprises from 90 mg to 300 mg of curcumin in an oral dose per day for an adult.

9. The agent according to claim 1, wherein the curcumin and the water-soluble cellulose derivative have a particle size of 300 μm or less.

10. The agent according to claim 1, wherein the agent has a content mass ratio of the curcumin to the water-soluble cellulose derivative of 0.1 to 570.

11. The agent according to claim 1, wherein the water-soluble cellulose derivative is hydroxypropyl methyl cellulose.

12. The method according to claim 5, wherein the curcumin and the water-soluble cellulose derivative have a particle size of 300 μm or less.

13. The method according to claim 5, wherein the agent has a content mass ratio of the curcumin to the water-soluble cellulose derivative of 0.1 to 570.

14. The method according to claim 5, wherein the water-soluble cellulose derivative is hydroxypropyl methyl cellulose.

* * * * *